United States Patent
Lee et al.

(10) Patent No.: US 10,922,874 B2
(45) Date of Patent: Feb. 16, 2021

(54) MEDICAL IMAGING APPARATUS AND METHOD OF DISPLAYING MEDICAL IMAGE

(71) Applicant: SAMSUNG MEDISON CO., LTD., Hongcheon-gun (KR)

(72) Inventors: Jin-yong Lee, Hongcheon-gun (KR); Sung-wook Park, Hongcheon-gun (KR); Jin-ki Park, Hongcheon-gun (KR); Joo-hyun Song, Hongcheon-gun (KR); Bong-heon Lee, Hongcheon-gun (KR); Hyuk-Jae Chang, Seoul (KR); Namsik Chung, Seoul (KR); Geu-ru Hong, Seoul (KR); Chi-young Shim, Seoul (KR); In-jeong Cho, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1086 days.

(21) Appl. No.: 14/929,547

(22) Filed: Nov. 2, 2015

(65) Prior Publication Data
US 2016/0125640 A1 May 5, 2016

(30) Foreign Application Priority Data
Oct. 31, 2014 (KR) .......... 10-2014-0150639

(51) Int. Cl.
*G06T 15/08* (2011.01)
*A61B 8/00* (2006.01)
(Continued)

(52) U.S. Cl.
CPC .............. *G06T 15/08* (2013.01); *A61B 8/463* (2013.01); *A61B 8/466* (2013.01); *A61B 8/469* (2013.01); *A61B 8/483* (2013.01); *A61B 8/5207* (2013.01); *G06T 19/00* (2013.01); *A61B 8/488* (2013.01); *A61B 8/523* (2013.01); *A61B 8/5238* (2013.01);
(Continued)

(58) Field of Classification Search
CPC ......... A61B 8/463; A61B 8/466; A61B 8/469; A61B 8/483; A61B 8/488; A61B 6/032; G01S 15/8993; G06T 15/08; G06T 19/00; G06T 2200/24; G06T 2210/41
See application file for complete search history.

(56) References Cited

U.S. PATENT DOCUMENTS 9,196,092 B2 * 11/2015 McDermott ............ G06T 15/08
9,247,922 B2 * 2/2016 Tsujita ..................... A61B 8/08
(Continued)

FOREIGN PATENT DOCUMENTS

JP     6-343632 A    12/1994
JP    2008-178500 A    8/2008

*Primary Examiner* — Baisakhi Roy
(74) *Attorney, Agent, or Firm* — Sughrue Mion, PLLC

(57) ABSTRACT

Provided is a medical imaging apparatus. The medical imaging apparatus includes: a user interface configured to receive an input for setting a region of interest (ROI) in a first medical image and an input for setting first volume rendering properties for the ROI and second volume rendering properties for a remaining region of the first medical image other than the ROI; an image generator configured to generate a second medical image by performing volume rendering on the ROI and the remaining region other than the ROI based on the first and second volume rendering properties, respectively; and a display configured to display the second medical image.

21 Claims, 11 Drawing Sheets

(51) Int. Cl.
  *A61B 5/00* (2006.01)
  *A61B 8/08* (2006.01)
  *G06T 15/04* (2011.01)
  *G06T 7/00* (2017.01)
  *G06T 19/00* (2011.01)

(52) U.S. Cl.
  CPC ...... *G06T 2200/24* (2013.01); *G06T 2210/41* (2013.01)

(56) References Cited

U.S. PATENT DOCUMENTS

| | | | |
|---|---|---|---|
| 9,986,969 B2* | 6/2018 | Call | A61B 8/14 |
| 2003/0016851 A1* | 1/2003 | Kaufman | A61B 6/032 |
| | | | 382/131 |
| 2003/0095697 A1* | 5/2003 | Wood | A61B 6/037 |
| | | | 382/131 |
| 2005/0271302 A1* | 12/2005 | Khamene | G06K 9/00986 |
| | | | 382/294 |
| 2008/0118131 A1* | 5/2008 | Skinner | G06T 7/0012 |
| | | | 382/131 |
| 2009/0003665 A1 | 1/2009 | Berg et al. | |
| 2009/0018448 A1 | 1/2009 | Seo et al. | |
| 2010/0185091 A1* | 7/2010 | Sumi | A61B 8/08 |
| | | | 600/443 |
| 2011/0069874 A1* | 3/2011 | Nagao | G06T 5/50 |
| | | | 382/128 |
| 2012/0243763 A1* | 9/2012 | Wen | G06T 5/50 |
| | | | 382/131 |
| 2016/0078668 A1* | 3/2016 | Wong | G06T 15/08 |
| | | | 345/424 |

* cited by examiner

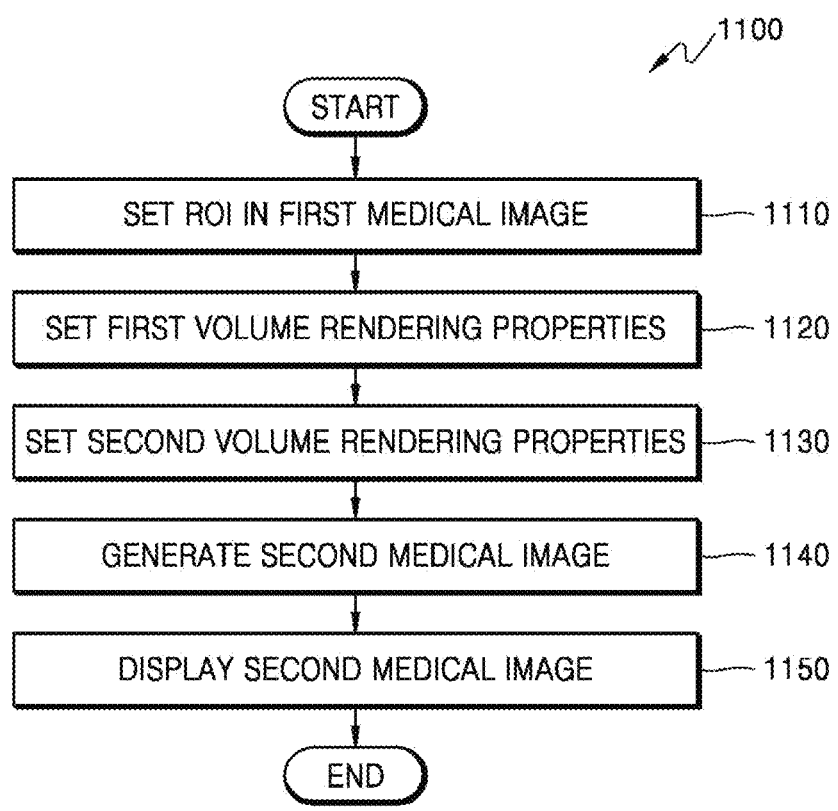

MEDICAL IMAGING APPARATUS AND METHOD OF DISPLAYING MEDICAL IMAGE

RELATED APPLICATION

This application claims the benefit of Korean Patent Application No. 10-2014-0150639, filed on Oct. 31, 2014, in the Korean Intellectual Property Office, the disclosure of which is incorporated herein in its entirety by reference.

BACKGROUND

1. Field

One or more exemplary embodiments relate to a medical imaging apparatus and a method of displaying a medical image.

2. Description of the Related Art

Medical imaging apparatuses are used to acquire images showing an internal structure of an object. The medical imaging apparatuses are non-invasive examination devices that capture and process images of details of structures, tissues, flow of fluid, etc., inside a body and provide the images to a user via a display. A user, e.g., a doctor may use medical images output from the medical imaging apparatuses to diagnose a patient's condition and disease.

Examples of medical imaging apparatuses may include ultrasound diagnosis apparatuses, computed tomography (CT) apparatuses, magnetic resonance imaging (MRI) apparatuses for providing MR images, and X-ray apparatuses.

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of an inner area of an object, detection of foreign substances, and diagnosis of damage to the object. Such ultrasound diagnosis apparatuses provide high stability, display images in real time, and are safe due to no radiation exposure, compared to X-ray apparatuses. Therefore, ultrasound diagnosis apparatuses are widely used together with other image diagnosis apparatuses including a CT apparatus, an MRI apparatus, and the like.

SUMMARY

One or more exemplary embodiments include a medical imaging apparatus and method of displaying a medical image by setting volume rendering properties for a region of interest (ROI) differently from those for the remaining region other than the ROI.

Additional aspects will be set forth in part in the description which follows and, in part, will be apparent from the description, or may be learned by practice of the presented exemplary embodiments.

According to one or more exemplary embodiments, a medical imaging apparatus includes: a user interface configured to receive an input for setting an ROI in a first medical image and an input for setting first volume rendering properties for the ROI and second volume rendering properties for a remaining region of the first medical image other than the ROI; an image generator configured to generate a second medical image by performing volume rendering on the ROI and the remaining region other than the ROI based on the first and second volume rendering properties, respectively; and a display configured to display the second medical image.

The image generator may perform the volume rendering on the ROI and the remaining region other than the ROI based on the first and second volume rendering properties, respectively, and synthesize a volume rendered medical image of the ROI with a volume rendered medical image of the remaining region other than the ROI, thereby generating the second medical image.

The second volume rendering properties may include transparency.

The second volume rendering properties may include a color map.

The second volume rendering properties may include properties for obtaining a contour of the remaining region.

At least one of the first and second volume rendering properties may be reset.

The second volume rendering properties may include at least one selected from the group consisting of a threshold, a gamma curve, a post gain, and an image filter.

The first volume rendering properties may include at least one selected from the group consisting of transparency, a color map, a threshold, a gamma curve, a post gain, and an image filter.

The first and second medical images may include a three-dimensional (3D) ultrasound image.

The medical imaging apparatus may further include a probe configured to transmit ultrasound signals to an object and receive ultrasound echo signals reflected from the object, and the image generator may generate the first medical image based on the received ultrasound echo signals.

According to one or more exemplary embodiments, a method of displaying a medical image includes: setting an ROI in a first medical image; setting first volume rendering properties for the ROI; setting second volume rendering properties for a remaining region of the first medical image other than the ROI; generating a second medical image by performing volume rendering on the ROI and the remaining region other than the ROI based on the first and second volume rendering properties, respectively, and displaying the second medical image.

In the generating of the second medical image, the second medical image may be generated by performing the volume rendering on the ROI and the remaining region other than the ROI based on the first and second volume rendering properties, respectively, and synthesizing a volume rendered medical image of the ROI with a volume rendered medical image of the remaining region other than the ROI.

The method may further include resetting at least one of the first and second volume rendering properties.

The method may further include: transmitting ultrasound signals to an object; receiving ultrasound echo signals reflected from the object; and generating the first medical image based on the received ultrasound echo signals.

According to one or more exemplary embodiments, a non-transitory computer-readable recording medium has recorded thereon a program for executing the method of displaying a medical image on a computer.

BRIEF DESCRIPTION OF THE DRAWINGS

These and/or other aspects will become apparent and more readily appreciated from the following description of the exemplary embodiments, taken in conjunction with the accompanying drawings in which:

FIG. 11 is a flowchart of a method of displaying a medical image according to an exemplary embodiment.

DETAILED DESCRIPTION

Figure 1:
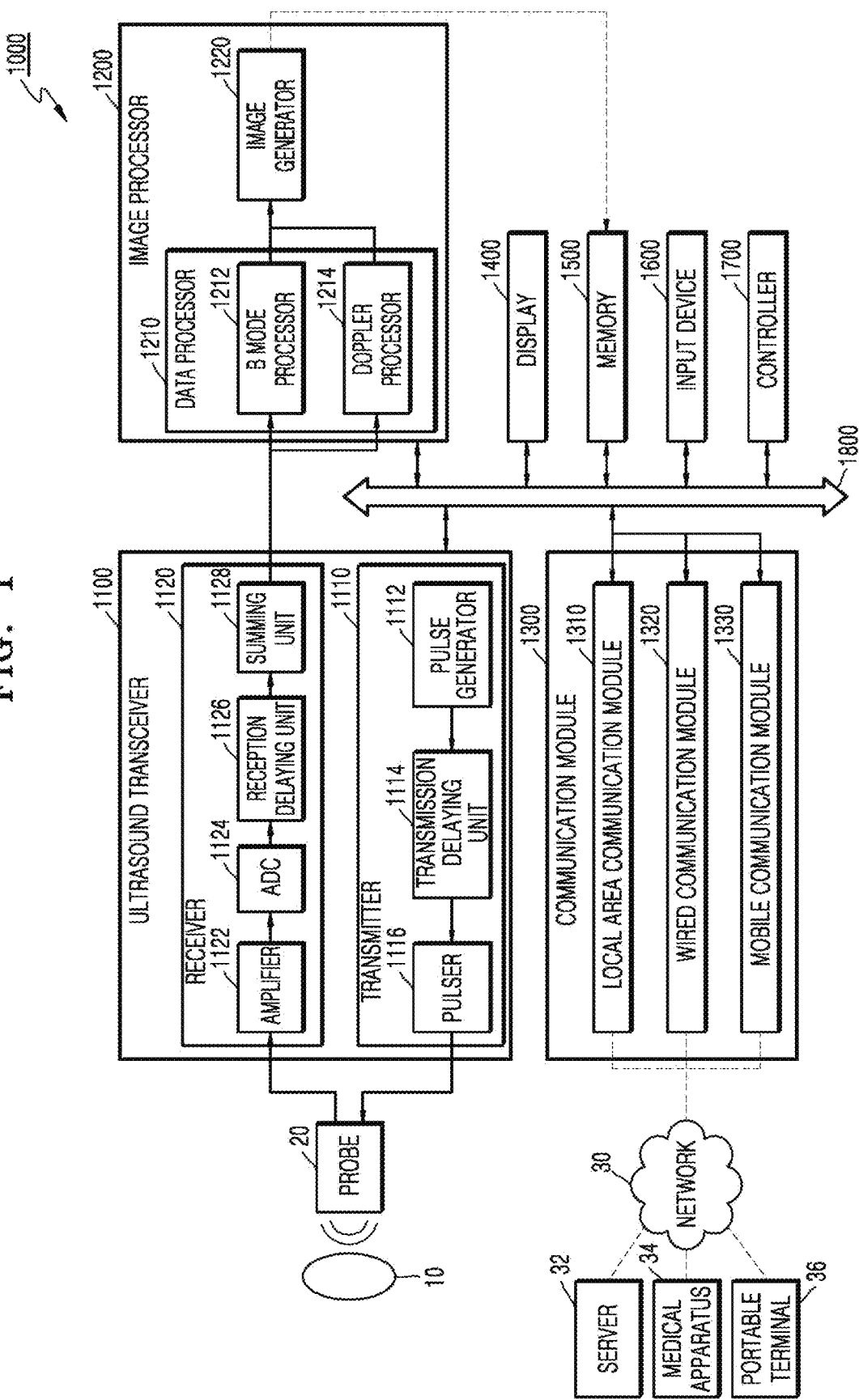
FIG. 1 is a block diagram of a configuration of an ultrasound diagnosis apparatus related to an exemplary embodiment.

Reference will now be made in detail to exemplary embodiments, examples of which are illustrated in the accompanying drawings, wherein like reference numerals refer to like structural elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

Advantages and features of one or more embodiments of the present invention and methods and apparatuses of accomplishing the same may be understood more readily by reference to the following detailed description of the embodiments and the accompanying drawings. The exemplary embodiments may, however, be embodied in many different forms and should not be construed as being limited to the embodiments set forth herein; rather, these embodiments are provided so that this disclosure will be thorough and complete, and will fully convey the concept of the exemplary embodiments to those skilled in the art.

Terms used herein will now be briefly described and then one or more exemplary embodiments will be described in detail.

General terms widely used are selected while considering functions in one or more exemplary embodiments for terms used herein, but the terms used herein may differ according to intentions of one of ordinary skill in the art, precedents, or emergence of new technologies. In some cases, an applicant arbitrarily selects a term, and in this case, the meaning of the term will be described in detail herein. Accordingly, the terms shall be defined based on the meanings and details throughout the specification, rather than the simple names of the terms.

Throughout the specification, it will also be understood that when a component "includes" an element, unless there is another opposite description thereto, it should be understood that the component does not exclude another element and may further include another element. The term "unit" used in the present specification refers to a software component, or a hardware component such as FPGA or ASIC, and performs a certain function. However, the term "unit" is not limited to software or hardware. The "unit" may be configured in an addressable storage medium and may be configured to be executed by one or more processors. Hence, the "unit" includes elements such as software elements, object-oriented software elements, class elements, and task elements, and processes, functions, attributes, procedures, sub-routines, segments of program codes, drivers, firmware, micro-codes, circuits, data, databases, data structures, tables, arrays, and variables. The functions provided in the elements and the units may be combined into a fewer number of elements and units or may be divided into a larger number of elements and units.

Reference will now be made in detail to embodiments, examples of which are illustrated in the accompanying drawings. In the following description, well-known functions or constructions are not described in detail so as not to obscure the embodiments with unnecessary detail.

In the present specification, "image" may refer to multi-dimensional data composed of discrete image elements (e.g., pixels in a two-dimensional image and voxels in a three-dimensional image). For example, an image may include a medical image of an object acquired by an ultrasonic waves, X-ray, computed tomography (CT), magnetic resonance imaging (MRI), or another medical image photographing apparatus Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the physical body.

Furthermore, throughout the specification, a "user" may be, but is not limited to, a medical expert, such as a medical doctor, a nurse, a medical laboratory technologist, a medical image expert, or a technician who repairs a medical apparatus.

In the present specification, an "ultrasound image" refers to an image of an object produced by using information of an echo signal that is reflected from the object when an ultrasound signal generated by transducers of a probe is transmitted to the object.

Throughout the specification, a "CT image" may mean an image generated by synthesizing a plurality of X-ray images that are obtained by photographing an object while a CT imaging apparatus rotates around at least one axis with respect to the object.

Furthermore, in the present specification, an "MR image" refers to an image of an object obtained by using the nuclear magnetic resonance principle.

Embodiments of the invention now will be described more fully hereinafter with reference to the accompanying drawings, in which illustrative embodiments of the invention are shown.

FIG. 1 is a block diagram showing a configuration of an ultrasound diagnosis apparatus 100 according to an embodiment. Referring to FIG. 1, the ultrasound diagnosis apparatus 100 may include a probe 20, an ultrasound transceiver 110, an image processor 200, a communication module 130, a display 140, a memory 150, an input device 160, and a controller 170, which may be connected to one another via buses 180.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 110 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly.

A transmitter 110 supplies a driving signal to the probe 20. The transmitter 1110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 1124 by delay times necessary for determining reception directionality, and the summing unit 128 generates ultrasound data by summing the echo signals processed by the reception delaying unit 1126. In some embodiments, the receiver 120 may not include the amplifier 122. In other words, if the sensitivity of the probe 20 or the capability of the ADC 124 to process bits is enhanced, the amplifier 122 may be omitted.

The image processor 200 generates an ultrasound image by scan-converting ultrasound data generated by the ultrasound transceiver 110 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 212 extracts B mode components from ultrasound data and processes the B mode components. An image generator 220 may generate an ultrasound image indicating signal intensities as brightness based on the extracted B mode components.

Similarly, a Doppler processor 214 may extract Doppler components from ultrasound data, and the image generator 220 may generate a Doppler image indicating a movement of an object as colors or waveforms based on the extracted Doppler components.

According to an embodiment, the image generator 220 may generate a three-dimensional (3D) ultrasound image via volume-rendering with respect to volume data and may also generate an elasticity image by imaging deformation of the object 10 due to pressure. Furthermore, the image generator 220 may display various pieces of additional information in an ultrasound image by using text and graphics. In addition, the generated ultrasound image may be stored in the memory 150.

A display 140 displays the generated ultrasound image. The display 140 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 140 according to embodiments.

The communication module 130 is connected to a network 30 by wire or wirelessly to communicate with an external device or a server. The communication module 130 may exchange data with a hospital server or another medical apparatus in a hospital, which is connected thereto via a PACS. Furthermore, the communication module 130 may perform data communication according to the digital imaging and communications in medicine (DICOM) standard.

The communication module 130 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 130 may receive information about a diagnosis history or medical treatment schedule of a patient from a server and utilizes the received information to diagnose the patient. Furthermore, the communication module 130 may perform data communication not only with a server or a medical apparatus in a hospital, but also with a portable terminal of a medical doctor or patient.

The communication module 130 is connected to the network 30 by wire or wirelessly to exchange data with a server 32, a medical apparatus 34, or a portable terminal 36. The communication module 130 may include one or more components for communication with external devices. For example, the communication module 1300 may include a local area communication module 131, a wired communication module 132, and a mobile communication module 133.

The local area communication module 131 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 132 refers to a module for communication using electric signals or optical signals. Examples of wired communication techniques according to an embodiment may include communication via a twisted pair cable, a coaxial cable, an optical fiber cable, and an Ethernet cable.

The mobile communication module 133 transmits or receives wireless signals to or from at least one selected from a base station, an external terminal, and a server on a mobile communication network. The wireless signals may be voice call signals, video call signals, or various types of data for transmission and reception of text/multimedia messages.

The memory 150 stores various data processed by the ultrasound diagnosis apparatus 100. For example, the memory 150 may store medical data related to diagnosis of an object, such as ultrasound data and an ultrasound image that are input or output, and may also store algorithms or programs which are to be executed in the ultrasound diagnosis apparatus 100.

The memory 150 may be any of various storage media, e.g., a flash memory, a hard disk drive, EEPROM, etc. Furthermore, the ultrasound diagnosis apparatus 100 may utilize web storage or a cloud server that performs the storage function of the memory 150 online.

The input device 160 refers to a means via which a user inputs data for controlling the ultrasound diagnosis apparatus 100. The input device 160 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 170 may control all operations of the ultrasound diagnosis apparatus 100. In other words, the controller 170 may control operations among the probe 20, the ultrasound transceiver 110, the image processor 200, the communication module 130, the display 140, the memory 150, and the input device 160 shown in FIG. 1.

All or some of the probe 20, the ultrasound transceiver 110, the image processor 200, the communication module 130, the display 140, the memory 150, the input device 160, and the controller 170 may be implemented as software modules. However, embodiments are not limited thereto, and some of the components stated above may be implemented as hardware modules. Furthermore, at least one selected from the ultrasound transceiver 110, the image processor 200, and the communication module 130 may be included in the controller 160. However, embodiments are not limited thereto.

Figure 2:
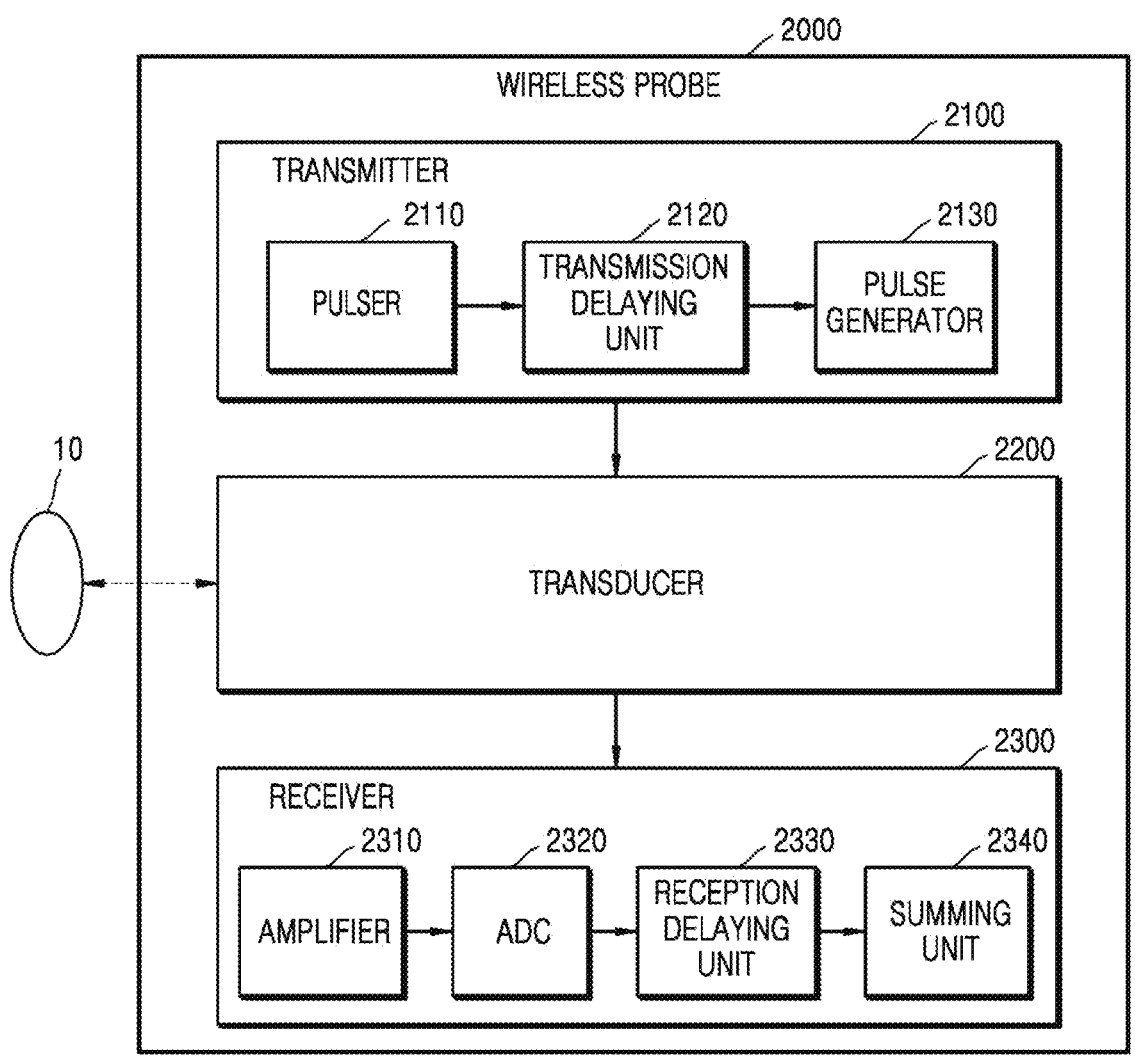
FIG. 2 is a block diagram of a configuration of a wireless probe related to an exemplary embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 100 shown in FIG. 1.

Figure 3:
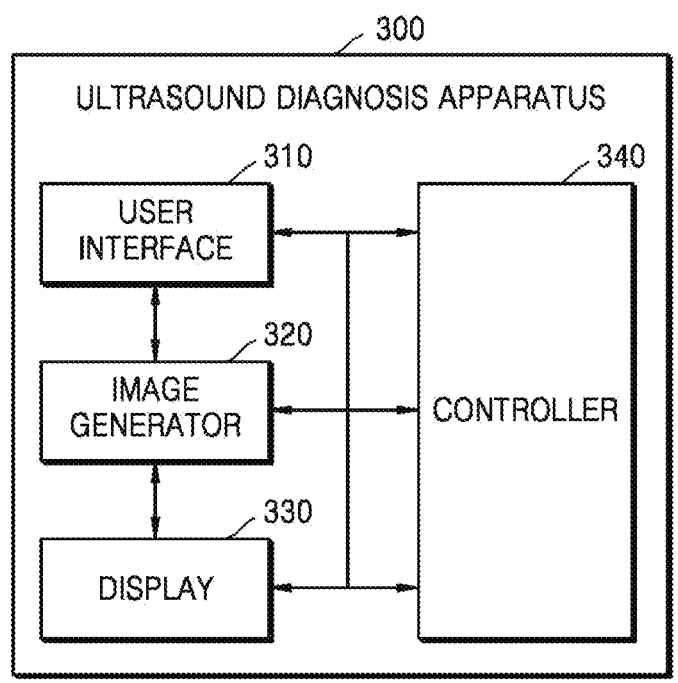
FIG. 3 is a block diagram of a configuration of a medical imaging apparatus according to an exemplary embodiment.

FIG. 3 is a block diagram of a configuration of a medical imaging apparatus 300 according to an exemplary embodiment.

When a user sets a region of interest (ROI), general medical imaging apparatuses may render and display only the ROI and crop images of the remaining region other than the ROI by using a cropping function. Thus, the user has difficulty in quickly identifying a relationship between the ROI and the whole object while performing a medical procedure.

To solve this problem and to efficiently perform a medical procedure, there is a need to provide a medical image that enables a user to quickly identify a relationship between an ROI and the entire object while analyzing the ROI. The medical imaging apparatus 300 according to the present exemplary embodiment is configured to display a medical image by setting volume rendering properties for an ROI differently from those of the remaining region other than the ROI, and will now be described in detail with reference to FIG. 3.

Referring to FIG. 3, the medical imaging apparatus 300 includes a user interface 310, an image generator 320, a display 330, and a controller 340.

As described above, the medical imaging apparatus 300 may be an ultrasound diagnosis apparatus, an MRI apparatus, a CT apparatus, an X-ray apparatus, or the like.

When the medical imaging apparatus 300 is included in the ultrasound diagnosis apparatus 1000 of FIG. 1, the user interface 310, the image generator 320, the display 330, and the controller 340 may correspond to or be included in the input device 160, the image generator 220, the display 140, and the controller 170, respectively. Thus, the same descriptions as already presented with respect to FIG. 1 are omitted.

The user interface 310 receives an input for setting an ROI in a first medical image of an object. In detail, the user interface 310 may allow a user to set as the ROI a portion of the first medical image that the user desires to scrutinize. For example, the user may set a cardiac valve in a medical image of the heart as an ROI.

In this case, medical image may include a 3D medical image. Examples of the first medical image may include a 3D ultrasound image, a 3D MR image, a 3D CT image, a 3D X-ray image, etc.

In detail, when the medical imaging apparatus 300 is included in the ultrasound diagnosis apparatus 100 of FIG. 1, the probe 20 may transmit ultrasound signals to the object 10 and receive ultrasound echo signals reflected from the object 10. The image generator 320 may then generate a 3D ultrasound image that is a first medical image based on the received ultrasound echo signals. Furthermore, the display 330 may display the 3D ultrasound image that is the first medical image.

The user interface 310 generates and outputs a user interface screen for receiving a predetermined command or data from a user and receives the predetermined command or data from the user via the user interface screen. The user interface screen output from the user interface 310 is also output to the display 330 that may in turn display the user interface screen. The user may then view the user interface screen displayed via the display 330 to recognize predetermined information and input a predetermined command or data.

For example, the user interface 310 may include a mouse, a keyboard, or another input device including hard keys for receiving predetermined data (or command). For example, the user may enter predetermined data or command by manipulating at least one of the mouse, the keyboard, and the other input device in the user interface 310.

In another example, the user interface 310 may be formed as a touch pad. In detail, the user interface 310 includes a touch pad (not shown) combined with a display panel (not shown) in the display 330 and outputs the user interface screen to the display panel. When a predetermined command is input via the user interface screen, the touch pad may detect the input or a pressure of the predetermined command, thereby recognizing the predetermined command input by the user.

In detail, if the user interface 310 is formed as a touch pad, when the user touches a predetermined point on the user interface screen, the user interface 310 detects a position of the touched point. The user interface 310 may then transmit information of the detected position to the image generator 320. The image generator 320 may then recognize a user request or command corresponding to a menu displayed at the detected position and generate a medical image according to the recognized user request or command.

The user interface 310 also receives an input for setting first volume rendering properties for an ROI. "Volume rendering properties" refer to predetermined conditions and parameters that are used for volume rendering to set a geometry and a texture of an object. For example, the volume rendering properties may include at least one selected from transparency, a color map, a threshold, a gamma curve, a post gain, and an image filter.

In detail, a color map may be color information of voxels. For example, the color map may include RGB information and grayscale information of voxels. A threshold may be the smallest magnitude of a medical image signal for distinguishing noise from the medical image signal. For example, among ultrasound signals received from the object, only ultrasound signals having magnitudes exceeding a threshold may be used for generating an ultrasound image. On the other hand, the remaining ultrasound signals having magnitudes not exceeding the threshold may not be used for generating an ultrasound image. A post gain may be a parameter for controlling a gain of a rendered medical image. An image filter may be predetermined filters for post-processing a rendered image.

However, the volume rendering properties are not limited thereto, and may further include effects of an external light source, shades, and a normal map, and the like.

Thus, the 'first volume rendering properties' refer to predetermined conditions and parameters for setting a geometry and texture information of the ROI. By setting the first volume rendering properties, the user may view the ROI in detail.

The user interface 310 receives an input for setting second volume rendering properties for the remaining region in the first medical image other than the ROI (hereinafter referred to as the 'remaining region'). In detail, the second volume rendering properties refer to predetermined conditions and parameters for setting a geometry and texture information of the remaining region.

For example, the medical imaging apparatus 300 may set the second volume rendering properties so that the remaining region may be semitransparent, appear as a black-and-white image, or has only a contour. Thus, by setting the second volume rendering properties, the user may use a medical image of the remaining region as reference information for quickly identifying the relationship between the ROI and the entire object.

The image generator 320 may generate a second medical image by performing volume rendering on the ROI and the remaining region based on the first and second volume rendering properties, respectively.

In detail, the image generator 320 performs volume rendering of volume data corresponding to the ROI based on the first volume rendering properties. The image generator 320 also performs volume rendering of the remaining region based on the second volume rendering properties. Thus, the ROI and the remaining region in the second medical image may have different volume rendering properties.

In detail, the image generator 320 may generate the second medical image by synthesizing volume rendered images of the ROI and the remaining region together. In this case, 'synthesis' may be an operation of combining corresponding parts of a plurality of medical images together or overlaying the plurality of medical images. For example, the image generator 320 may determine positions of the ROI and the remaining region by using coordinates of the first medical image and combine or overlay together volume rendered medical images of the ROI and the remaining region.

The display 330 may display the second medical image. As described above, the ROI and the remaining region in the second medical image may have different volume rendering properties. Thus, the medical imaging apparatus 300 may provide a medical image with a visually enhanced ROI and encompassing the entire object to the user. Furthermore, by viewing the displayed second medical image, the user may quickly identify the relationship between the ROI and the entire object while viewing in detail the ROI.

Figure 4:
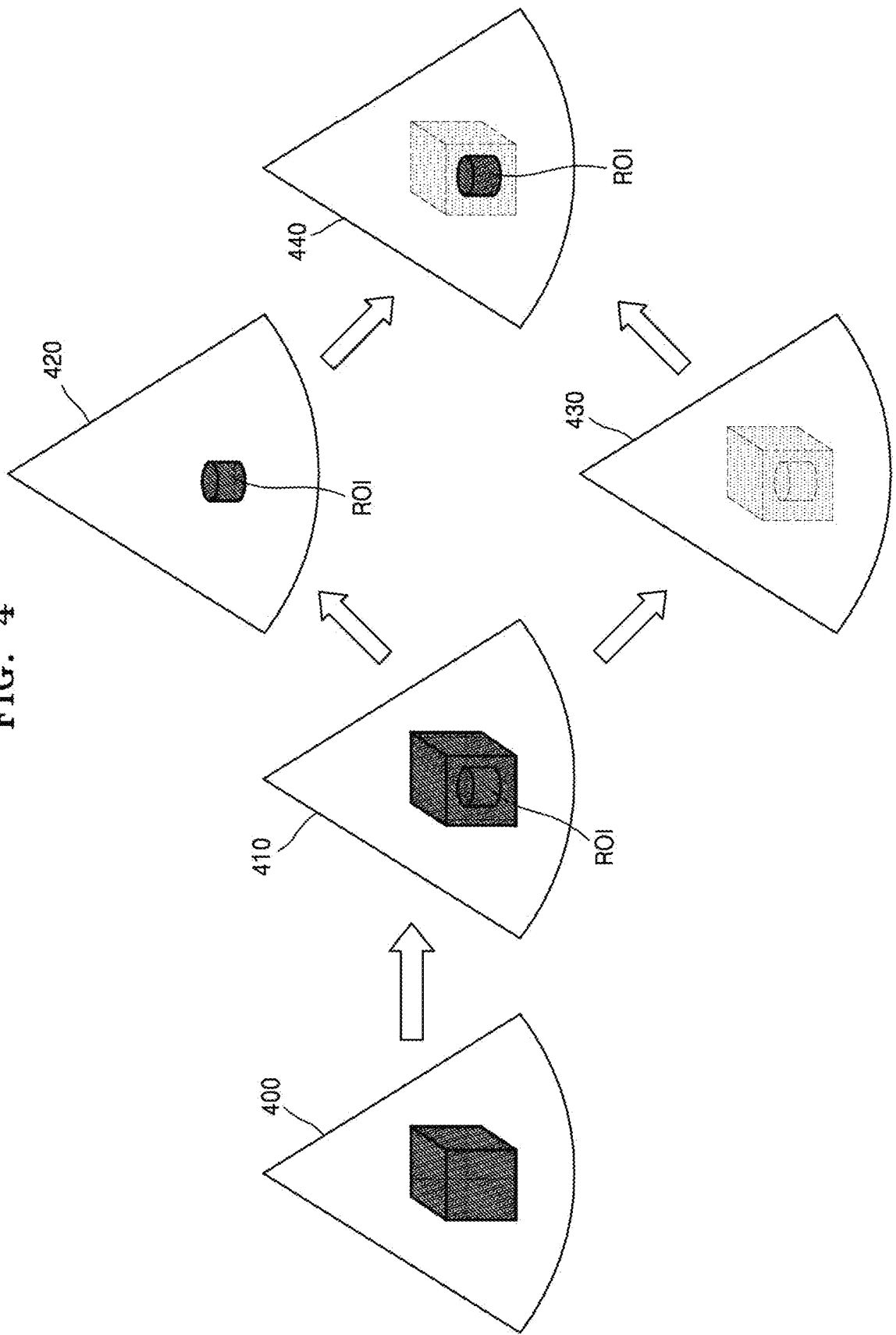
FIG. 4 is a conceptual diagram for explaining an operation of displaying a medical image by a medical imaging apparatus according to an exemplary embodiment.

FIG. 4 is a conceptual diagram for explaining an operation of displaying a medical image by the medical imaging apparatus 300 of FIG. 3 according to an exemplary embodiment. In detail, FIG. 4 sequentially illustrates a process of generating a second medical image 440 from a first medical image 400.

400 denotes the first medical image. For example, the image generator 320 may generate the first medical image 400 of an object having a square shape.

410 denotes an image in which an ROI is set in the first medical image 400. For example, the user interface 310 may receive an input for setting the ROI having a cylindrical shape within the object.

420 denotes a volume rendered medical image of the ROI generated based on first volume rendering properties. For example, the image generator 320 may perform volume rendering on the ROI to obtain a color image of the ROI based on a color map that is one of the first volume rendering properties.

430 denotes a volume rendered medical image of the remaining region other than the ROI, which is generated based on second volume rendering properties. For example, the image generator 320 may perform volume rendering on the remaining region other than the ROI in a semi-transparent way based on transparency that is one of the second volume rendering properties.

440 represents the second medical image. In detail, the image generator 320 may generate the second medical image 440 by synthesizing the volume rendered medical image 420 of the ROI with the volume rendered medical image 430 of the remaining region other than the ROI. For example, the second medical image 440 may include a semitransparent square and a colored cylinder located therein.

Figure 5:
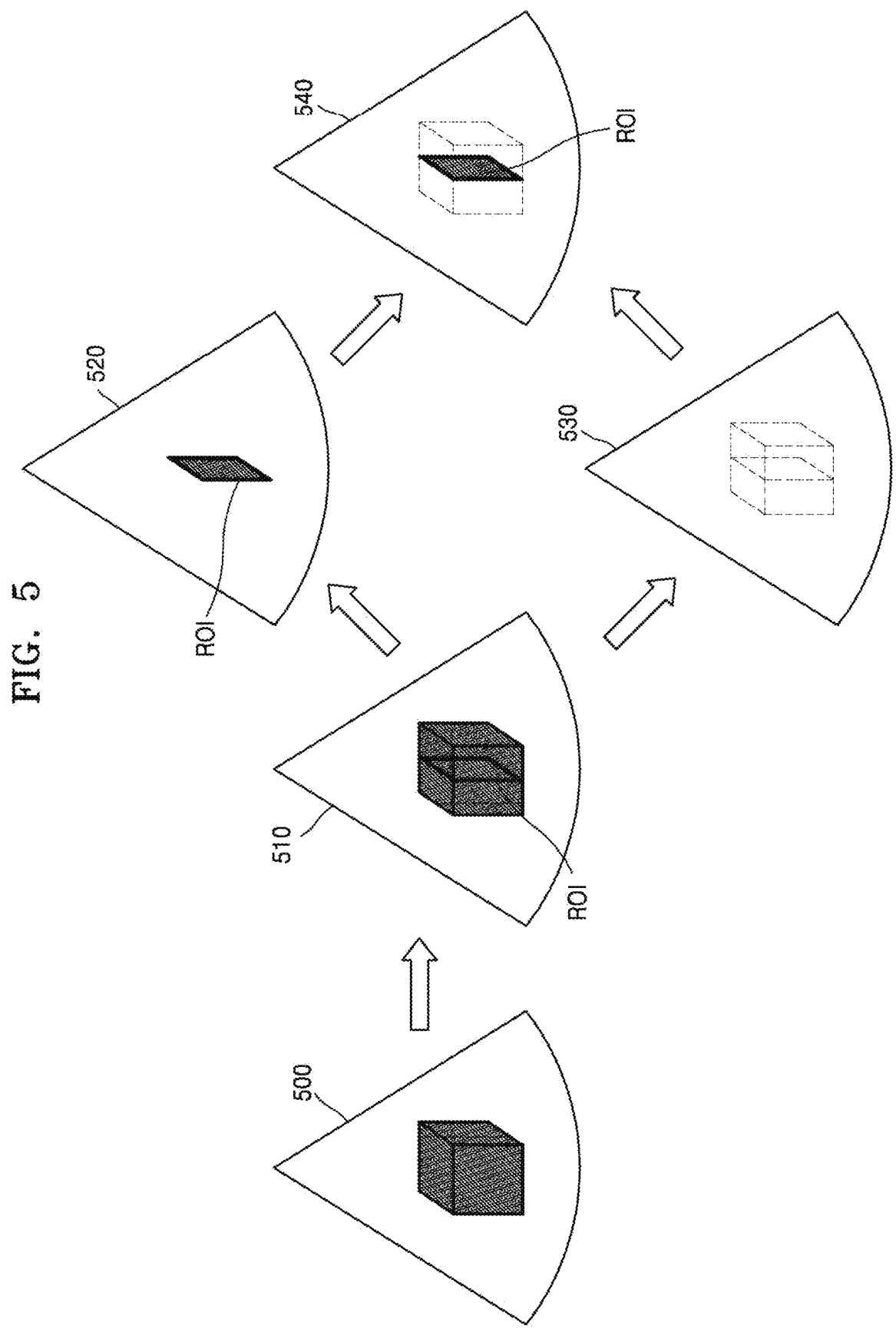
FIG. 5 is a conceptual diagram for explaining an operation of displaying a medical image by a medical imaging apparatus according to another exemplary embodiment.

FIG. 5 is a conceptual diagram for explaining an operation of displaying a medical image by the medical imaging apparatus 300 of FIG. 3 according to another exemplary embodiment. In detail, FIG. 5 sequentially illustrates a process of generating a second medical image 540 from a first medical image 500.

500 denotes the first medical image. For example, the image generator 320 may generate the first medical image 500 of an object having a square shape.

510 denotes a medical image in which an ROI is set in the first medical image 500. For example, the user interface 310 may receive an input for setting a predetermined cross-section of the object as the ROI.

520 denotes a volume rendered medical image of the ROI generated based on first volume rendering properties. For example, the image generator 320 may perform volume rendering on the ROI to obtain a color image of the ROI based on a color map that is one of the first volume rendering properties.

530 denotes a volume rendered medical image of the remaining region other than the ROI, which is generated based on second volume rendering properties. The second volume rendering properties may include properties for obtaining a contour of an image, such as gradient and laplacian. For example, the image generator 320 may obtain a contour of the remaining region other than the ROI based on a gradient of volume data.

540 represents the second medical image. In detail, the image generator 320 may generate the second medical image 540 by synthesizing the volume rendered medical image 520 of the ROI with the volume rendered medical image 530 of the remaining region other than the ROI. Thus, the second medical image 540 may include a contour of a square and the cross-section of the square represented by a color texture.

As described above, by viewing the second medical images 440 and 540 respectively shown in FIGS. 4 and 5, the user may quickly identify the relationship between the ROI and the entire object while simultaneously observing the ROI in an intensive way. For example, the user may identify the position, function, etc. of the ROI with respect to the object via the second medical images 440 and 540.

Operations of the medical imaging apparatus (300 of FIG. 3) for displaying a 3D ultrasound image will now be described in detail with reference to FIGS. 6 through 10.

Figure 6:
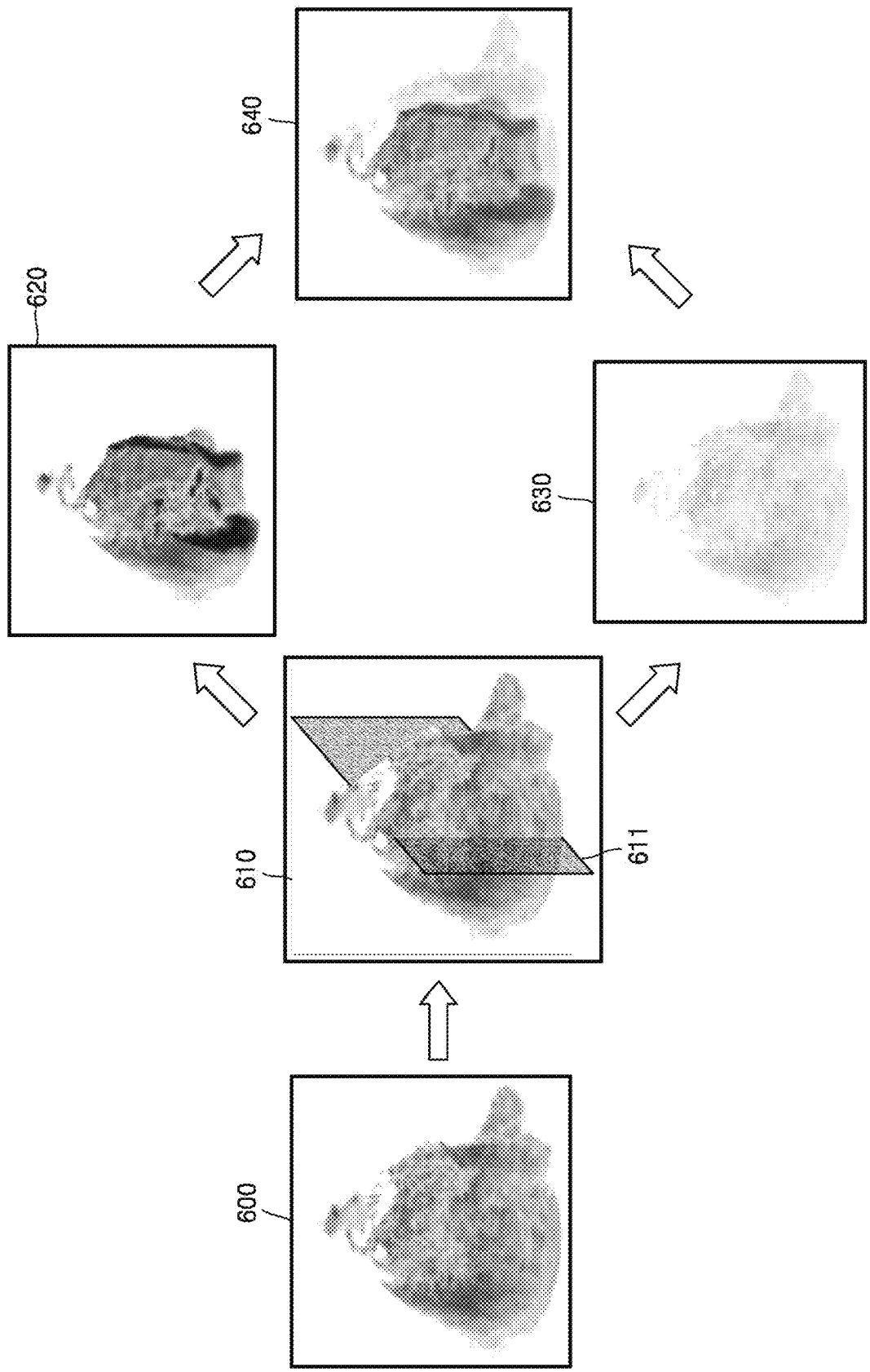
FIG. 6 is a diagram for explaining an operation of displaying a three-dimensional (3D) ultrasound image of the heart by a medical imaging apparatus according to an exemplary embodiment.

FIG. 6 is a diagram for explaining an operation of displaying a 3D ultrasound image of the heart by the medical imaging apparatus 300 according to an exemplary embodiment. In detail, FIG. 6 sequentially illustrates a process of generating a second ultrasound image 640 from a first ultrasound image 600 of a left ventricle.

600 denotes the first ultrasound image. In detail, when the medical imaging apparatus 300 is included in the ultrasound diagnosis apparatus 100 of FIG. 1, the probe 20 may transmit ultrasound signals to the left ventricle and receive ultrasound echo signals reflected from the left ventricle. The image generator 320 may then generate the first ultrasound image 600 that is a 3D ultrasound image based on the received ultrasound echo signals.

610 denotes an ultrasound image in which an ROI is set in the first ultrasound image 600. In detail, the user interface 310 may receive an input for setting a portion of the left ventricle obtained by cutting the left ventricle along a predetermined plane 611 as the ROI.

620 denotes a volume rendered ultrasound image of the ROI generated based on first volume rendering properties. In detail, the image generator 320 may generate a color image of the portion of the left ventricle set as the ROI, based on the first volume rendering properties. The volume rendered ultrasound image 620 of the ROI will be described in more detail below with reference to FIG. 7.

630 denotes a volume rendered ultrasound image of the remaining region other than the ROI, which is generated based on second volume rendering properties. In detail, the image generator 320 may generate a semitransparent grayscale image of the remaining portion of the left ventricle that is not set as the ROI, based on the second volume rendering properties. The volume rendered ultrasound image 630 will be described in more detail below with reference to FIG. 8.

640 represents the second ultrasound image. For example, the image generator 320 may generate the second ultrasound image 640 by synthesizing the volume rendered ultrasound image 620 of the ROI with the volume rendered ultrasound image 630 of the remaining region other than the ROI. In detail, the second ultrasound image 640 may include the color image of the portion of the left ventricle corresponding to the ROI and the semitransparent grayscale image of the remaining portion thereof.

Figure 7:
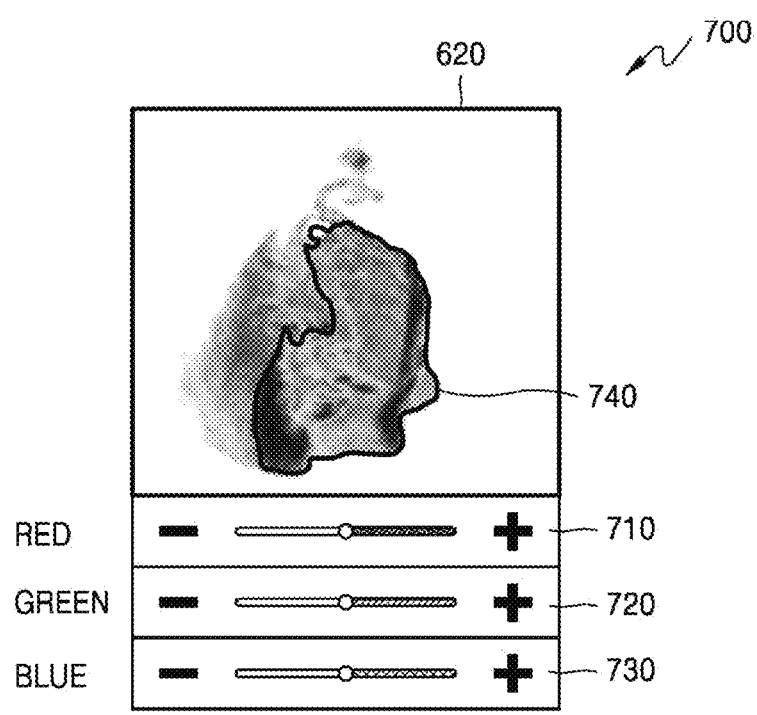
FIG. 7 is a diagram for explaining an operation of setting first volume rendering properties by a medical imaging apparatus according to an exemplary embodiment.

FIG. 7 is a diagram for explaining an operation of setting the first volume rendering properties by the medical imaging apparatus 300 according to an exemplary embodiment.

FIG. 7 shows the volume rendered ultrasound image 620 of the ROI shown in FIG. 6. In detail, the ROI corresponds to the portion of the left ventricle obtained by cutting the left ventricle along the predetermined plane 611. For convenience, a contour of a cross-section obtained by cutting the left ventricle by the predetermined plane 611 is indicated by a bold line 740.

After the ROI is set, the display 330 may display a user interface screen for setting the first volume rendering properties.

For example, the display unit 330 may display a user interface screen 700 for setting RGB information of the ROI. In detail, the user interface screen 700 may include slide bars 710, 720, and 730 for setting the RGB information of the ROI. Alternatively, the display 330 may display a user interface screen for setting a post gain and an image filter for the ROI.

Figure 8:
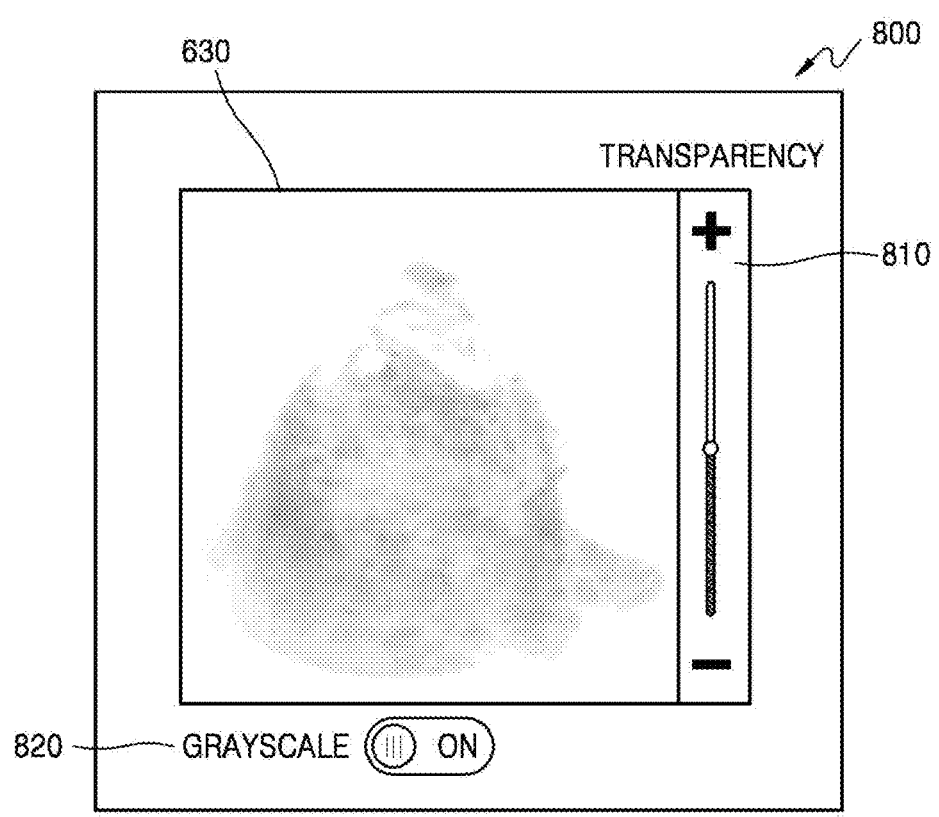
FIG. 8 is a diagram for explaining an operation of setting second volume rendering properties performed by a medical imaging apparatus according to an exemplary embodiment.

FIG. 8 is a diagram for explaining an operation of setting second volume rendering properties by the medical imaging apparatus 300 according to an exemplary embodiment. FIG. 8 shows the volume rendered ultrasound image 630 of the remaining region other than the ROI shown in FIG. 6.

After the ROI is set, the display 330 may display a user interface screen for setting the second volume rendering properties.

For example, the display unit 330 may display a user interface screen 800 for setting the second volume rendering properties, i.e., transparency and a grayscale mode. In detail, the user interface screen 800 may include a slide bar 810 for adjusting the transparency of the remaining region other than the ROI. Alternatively, the display 330 may display a user interface screen for setting a post gain and an image filter for the ROI. The user interface screen 800 may include a switch 820 for setting the remaining region other than the ROI to the grayscale mode. Referring to FIG. 8, the remaining portion of the left ventricle that is not set as the ROI is displayed as a semitransparent grayscale image.

Figure 9:
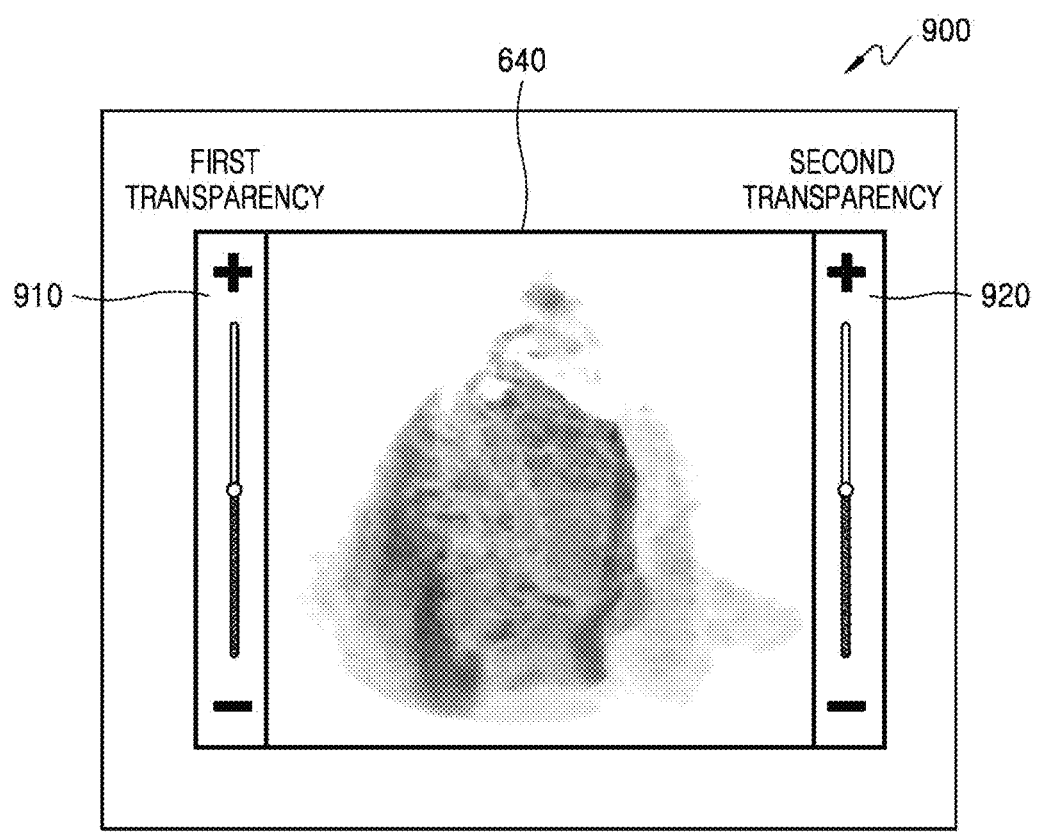
FIG. 9 is a diagram for explaining an operation of setting first and second volume rendering properties by a medical imaging apparatus according to an exemplary embodiment.

FIG. 9 is a diagram for explaining an operation of setting first and second volume rendering properties by the medical imaging apparatus 300 according to an exemplary embodiment.

FIG. 9 shows the second ultrasound image 640 generated by synthesizing the volume rendered ultrasound image 620 of the ROI with the volume rendered ultrasound image 630 of the remaining region other than the ROI. In detail, the ROI in the second ultrasound image 640 of the left ventricle is rendered as a color image while the remaining region other than the ROI is rendered as a semitransparent black-and-white image.

After the ROI is set, the display 330 may display a user interface screen for setting the first and second volume rendering properties.

For example, the display 330 may display a user interface screen 900 for setting transparencies that are the first and second volume rendering properties. In detail, the user interface screen 900 may include slide bars 910 and 920 for respectively setting first and second transparencies of the ROI and the remaining region other than the ROI.

Furthermore, the medical imaging apparatus 300 may reset at least one of the first and second volume rendering properties. In detail, the medical imaging apparatus 300 may set the first and second volume rendering properties even after generating the second ultrasound image 640 as well as before generating the same.

Thus, the user may reset at least one of the first and second volume rendering properties while performing a medical procedure. For example, the user may reduce the second transparency that is one of the second volume rendering properties in order to identify the relationship between the ROI and the entire object while performing a medical procedure, or increase the second transparency in order to further scrutinize the ROI.

Figure 10:
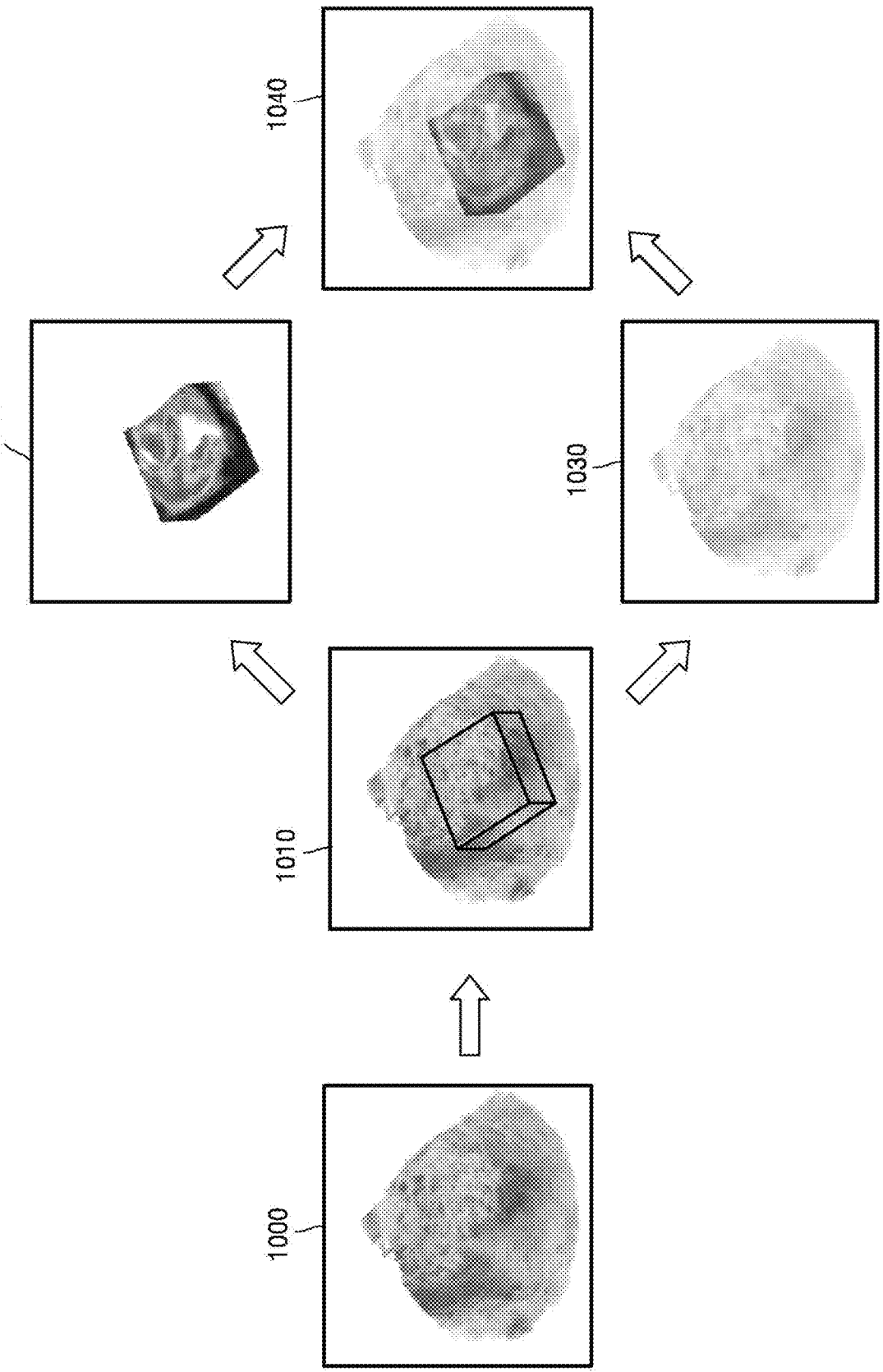
FIG. 10 is a diagram for explaining an operation of displaying a 3D ultrasound image of the heart by a medical imaging apparatus according to another exemplary embodiment.

FIG. 10 is a diagram for explaining an operation of displaying a 3D ultrasound image of the heart by the medical imaging apparatus 300 according to another exemplary embodiment. In detail, FIG. 10 sequentially illustrates a process of generating a second ultrasound image 1040 from a first ultrasound image 1000 including a cardiac valve.

1000 denotes the first ultrasound image. In detail, when the medical imaging apparatus 300 is included in the ultrasound diagnosis apparatus 100 of FIG. 1, the probe 20 may transmit ultrasound signals to the heart and receive ultrasound echo signals reflected from the heart. The image generator 320 may then generate the first medical image 1000 that is a 3D ultrasound image based on the received ultrasound echo signals.

1010 denotes an ultrasound image in which an ROI is set in the first ultrasound image 1000. In detail, the user interface 310 may receive an input for setting the cardiac valve as the ROI.

1020 denotes a volume rendered ultrasound image of the ROI generated based on first volume rendering properties. In detail, the image generator 320 may generate a color ultrasound image of the cardiac valve based on the first volume rendering properties. The image generator 320 may also control a gain for the color ultrasound image of the cardiac valve. The medical imaging apparatus 300 may visually enhance the cardiac valve in the volume rendered ultrasound image 1020 for display, according to the first volume rendering properties.

1030 denotes a volume rendered ultrasound image of the remaining region other than the ROI, which is generated based on second volume rendering properties. In detail, the image generator 320 may generate a semitransparent grayscale image of the remaining portion of the heart that is not set as the ROI, based on the second volume rendering properties.

1040 represents the second ultrasound image. For example, the image generator 320 may generate the second ultrasound image 640 by synthesizing the volume rendered ultrasound image 1020 of the ROI with the volume rendered ultrasound image 1030 of the remaining region other than the ROI. In detail, the second ultrasound image 1040 may include the color image of the cardiac valve corresponding to the ROI and the semitransparent grayscale image of the remaining portion of the heart.

According to the exemplary embodiment, through the second ultrasound image 1040, the user may detect the position of the cardiac valve by referring to the whole image of the heart while scrutinizing the cardiac valve.

FIG. 11 is a flowchart of a method 1100 of displaying a medical image according to an exemplary embodiment. The method 1100 may include the same operations as those performed by the medical imaging apparatus 300 described above with reference to FIGS. 1 through 10. Thus, in describing the method 1100, the same descriptions as already presented with respect to FIGS. 1 through 10 are omitted.

Referring to FIGS. 3 and 11, according to the method 1100, an ROI is set in a first medical image (operation 1100). Operation 1100 may be performed by the user interface 310.

In this case, the medical image may include a 3D ultrasound image, a 3D MR image, a 3D CT image, a 3D X-ray image, and the like. For example, the method 1100 may include transmitting ultrasound signals to an object, receiving ultrasound echo signals reflected from the object, and generating a 3D ultrasound image that is the first medical image based on the received ultrasound echo signals.

According to the method 1100, first volume rendering properties are set for the ROI that is set in operation 1110 (operation 1120). In detail, the first volume rendering properties refer to predetermined conditions and parameters for setting a geometry and texture information of the ROI. For example, the first volume rendering properties may include at least one selected from transparency, a color map, a threshold, a gamma curve, a post gain, and an image filter. Operation 1120 may be performed by the user interface 310.

According to the method 1100, second volume rendering properties are set for the remaining region other than the ROI (operation 1130). The second volume rendering properties are predetermined conditions and parameters for setting a geometry and texture information of the remaining region other than the ROI. For example, the second volume rendering properties may include at least one selected from transparency, a color map, a threshold, a gamma curve, a post gain, and an image filter. The second volume rendering properties may further include properties for obtaining an image contour, such as gradient and laplacian. Operation 1130 may be performed by the user interface 310.

The method 1100 may further include resetting at least one of the first and second volume rendering properties. In detail, according to the method 1100, the first and second volume rendering properties may be set even after a second medical image is generated.

According to the method 1100, a second medical image is generated by performing volume rendering on the ROI and the remaining region other than the ROI based on the first and second volume rendering properties, respectively (operation 1140). In detail, the second medical image may be generated by synthesizing a volume rendered medical image of the ROI with a volume rendered medical image of the remaining region other than the ROI. Operation 1140 may be performed by the image generator 320.

According to the method 1100, the second medical image generated in operation 1140 may be displayed (operation 1150). Operation 1150 may be performed by the display 330.

As described above, a medical imaging apparatus and a method of displaying a medical image according to exemplary embodiments are capable of setting volume rendering properties for an ROI differently from those for the remaining region other than the ROI.

Thus, the medical imaging apparatus and method of displaying a medical image allow display of a medical image that represents the relationship between an ROI and the entire object while simultaneously visually enhancing the ROI.

The exemplary embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A medical imaging apparatus comprising:
   a user interface configured to receive an input for setting a region of interest (ROI) in a first medical image and an input for setting first volume rendering properties for the ROI and second volume rendering properties for a remaining region of the first medical image, wherein the remaining region is identified as a region other than the ROI set by a user in the first medical image;
   a display; and
   one or more processors configured to generate a second medical image by performing volume rendering on the ROI and the remaining region other than the ROI based on the first and second volume rendering properties, respectively, and control the display to display the second medical image,
   wherein the one or more processors are further configured to:
      display the ROI in the first medical image and at least one item related to the first volume rendering properties via the display, and receive the input for setting the first volume rendering properties via the user interface while displaying the first medical image and the at least one item related to the first volume rendering properties, and
      display the remaining region of the first medical image and at least one item related to the second volume rendering properties via the display, and receive the input for setting the second volume rendering properties via the user interface while displaying the second medical image and the at least one item related to the second volume rendering properties.

2. The medical imaging apparatus of claim 1, wherein the one or more processors perform the volume rendering on the ROI and the remaining region other than the ROI based on the first and second volume rendering properties, respectively, and synthesize a volume rendered medical image of the ROI with a volume rendered medical image of the remaining region other than the ROI, thereby generating the second medical image.

3. The medical imaging apparatus of claim 1, wherein the second volume rendering properties comprise transparency.

4. The medical imaging apparatus of claim 1, wherein the second volume rendering properties comprise a color map.

5. The medical imaging apparatus of claim 1, wherein the second volume rendering properties comprise properties for obtaining a contour of the remaining region.

6. The medical imaging apparatus of claim 1, wherein at least one of the first and second volume rendering properties is reset.

7. The medical imaging apparatus of claim 1, wherein the second volume rendering properties comprise at least one selected from the group consisting of a threshold, a gamma curve, a post gain, and an image filter.

8. The medical imaging apparatus of claim 1, wherein the first volume rendering properties comprise at least one selected from the group consisting of transparency, a color map, a threshold, a gamma curve, a post gain, and an image filter.

9. The medical imaging apparatus of claim 1, wherein the first and second medical images comprise a three-dimensional (3D) ultrasound image.

10. The medical imaging apparatus of claim 9, further comprising a probe configured to transmit ultrasound signals to an object and receive ultrasound echo signals reflected from the object,
    wherein the one or more processors generate the first medical image based on the received ultrasound echo signals.

11. A method of displaying a medical image, the method comprising:
    setting a region of interest (ROI) in a first medical image;
    setting first volume rendering properties for the ROI;
    setting second volume rendering properties for a remaining region of the first medical image, wherein the remaining region is identified as a region other than the ROI set by a user in the first medical image;
    generating a second medical image by performing volume rendering on the ROI and the remaining region other than the ROI based on the first and second volume rendering properties, respectively; and
    displaying the second medical image,
    wherein the setting of the first volume rendering properties comprises:
       displaying the ROI in the first medical image and at least one item related to the first volume rendering properties via the display, and
       receiving the input for setting the first volume rendering properties via the user interface while displaying the first medical image and the at least one item related to the first volume rendering properties, and
    wherein the setting of the second volume rendering properties comprises:
       displaying the remaining region of the first medical image and at least one item related to the second volume rendering properties via the display, and
       receiving the input for setting the second volume rendering properties via the user interface while displaying the second medical image and the at least one item related to the second volume rendering properties.

12. The method of claim 11, wherein in the generating of the second medical image, the second medical image is generated by performing the volume rendering on the ROI and the remaining region other than the ROI based on the first and second volume rendering properties, respectively, and synthesizing a volume rendered medical image of the ROI with a volume rendered medical image of the remaining region other than the ROI.

13. The method of claim 11, wherein the second volume rendering properties comprise transparency.

14. The method of claim 11, wherein the second volume rendering properties comprise a color map.

15. The method of claim 11, wherein the second volume rendering properties comprise properties for obtaining a contour of the remaining region.

16. The method of claim 11, further comprising resetting at least one of the first and second volume rendering properties.

17. The method of claim 11, wherein the second volume rendering properties comprise at least one selected from the group consisting of a threshold, a gamma curve, a post gain, and an image filter.

18. The method of claim 11, wherein the first volume rendering properties comprise at least one selected from the group consisting of transparency, a color map, a threshold, a gamma curve, a post gain, and an image filter.

19. The method of claim 11, wherein the first and second medical images comprise a three-dimensional (3D) ultrasound image.

20. The method of claim 19, further comprising:
transmitting ultrasound signals to an object;
receiving ultrasound echo signals reflected from the object; and
generating the first medical image based on the received ultrasound echo signals.

21. A non-transitory computer-readable recording medium having recorded thereon a program for executing the method of claim 11.

* * * * *